United States Patent
Sommers et al.

(10) Patent No.: US 10,610,243 B2
(45) Date of Patent: Apr. 7, 2020

(54) SYSTEM AND METHOD FOR INSTALLING A BICORTICAL IMPLANT IN BONE

(71) Applicant: Acumed LLC, Hillsboro, OR (US)

(72) Inventors: Mark B. Sommers, Beaverton, OR (US); Roy Werner Sanders, Tampa, FL (US); James G. Falkner, Jr., Beaverton, OR (US); Caleb Abraham Martin, Beaverton, OR (US); Zachary James Stroh, Hillsboro, OR (US)

(73) Assignee: Acumed LLC, Hillsboro, OR (US)

( * ) Notice: Subject to any disclaimer, the term of this patent is extended or adjusted under 35 U.S.C. 154(b) by 242 days.

(21) Appl. No.: 15/728,247

(22) Filed: Oct. 9, 2017

(65) Prior Publication Data

US 2019/0105060 A1    Apr. 11, 2019

(51) Int. Cl.
*A61B 17/16*    (2006.01)
*A61B 17/86*    (2006.01)
(Continued)

(52) U.S. Cl.
CPC .......... *A61B 17/1615* (2013.01); *A61B 17/72* (2013.01); *A61B 17/8625* (2013.01);
(Continued)

(58) Field of Classification Search
CPC . A61B 17/1615; A61B 17/72; A61B 17/8625; A61B 17/8645; A61B 17/0401;
(Continued)

(56) References Cited

U.S. PATENT DOCUMENTS

| 2,391,396 | A |   | 12/1945 | Denison |
| 3,495,483 | A | * | 2/1970  | Janik ................. B23B 5/167 408/211 |

(Continued)

FOREIGN PATENT DOCUMENTS

| CN | 105686860 A  | 6/2016  |
| EP | 1712194 A1   | 10/2006 |

(Continued)

OTHER PUBLICATIONS

ANCA CNC Machines, "5 Practical Steps to Making Rotary Instruments that Surgeons Want to Use—Step 2" brochure, Jun. 25, 2012, 8 pgs.

(Continued)

*Primary Examiner* — David W Bates
*Assistant Examiner* — Marcela I. Shirsat
(74) *Attorney, Agent, or Firm* — Kolisch Hartwell, P.C.

(57) ABSTRACT

Orthopedic systems and methods for installing an implant and/or boring a bone bicortically. The system may include a drill having a proximal boring portion configured to bore a larger hole in a bone more efficiently when the drill rotates in a first direction compared to an opposite second direction, and a distal boring portion configured to bore a smaller hole in the bone more efficiently when the drill rotates in the second direction. The implant may be configured to be implanted at least partially in the bone, such that a first region of the implant is located in the larger hole and a second region of the implant is located in the smaller hole. In an exemplary method, the larger hole and the smaller hole may be bored in the bone's near cortex and far cortex, respectively, by a shaft and a nose of the drill rotated in opposite directions.

15 Claims, 8 Drawing Sheets

(51) Int. Cl.
*A61B 17/72* (2006.01)
*B23B 51/02* (2006.01)

(52) U.S. Cl.
CPC .......... *A61B 17/8645* (2013.01); *B23B 51/02* (2013.01); *B23B 2251/14* (2013.01); *B23B 2251/18* (2013.01); *B23B 2251/60* (2013.01)

(58) Field of Classification Search
CPC ...... A61B 2017/0414; A61B 2017/044; A61B 2017/0445; A61B 2017/0438; A61B 2017/045; A61B 2017/0464; B23B 51/02; B23B 2251/14; B23B 2251/18; B23B 2251/201; B23B 2251/204; B23B 2251/60
USPC ......... 606/309; 408/199, 202, 227, 230, 147
See application file for complete search history.

(56) References Cited

U.S. PATENT DOCUMENTS

| | | | |
|---|---|---|---|
| 3,913,196 A * | 10/1975 | Maday | B23B 51/08 407/54 |
| 4,507,028 A * | 3/1985 | Matsushita | B23B 51/08 408/227 |
| 4,738,255 A * | 4/1988 | Goble | A61B 17/0401 29/243.519 |
| 4,978,350 A * | 12/1990 | Wagenknecht | A61B 17/8635 411/387.7 |
| 5,000,630 A * | 3/1991 | Riley | B23B 51/00 407/1 |
| 5,129,901 A | 7/1992 | Decoste | |
| 5,456,267 A | 10/1995 | Stark | |
| 5,573,537 A * | 11/1996 | Rogozinski | A61B 17/1671 408/225 |
| 5,947,659 A | 9/1999 | Mays | |
| 6,197,031 B1 | 3/2001 | Barrette et al. | |
| 6,267,542 B1 | 7/2001 | Salmon | |
| 6,641,395 B2 | 11/2003 | Kumar et al. | |
| 6,890,133 B2 | 5/2005 | Singh et al. | |
| 7,137,462 B2 | 11/2006 | Miyanaga | |
| 7,267,514 B2 | 11/2007 | Wetzl et al. | |
| 7,665,935 B1 | 2/2010 | Garrick et al. | |
| 7,717,945 B2 | 5/2010 | Jensen et al. | |
| 7,892,235 B2 | 2/2011 | Ellis | |
| 8,162,945 B2 | 4/2012 | Ellis | |
| 8,172,845 B2 | 5/2012 | Ellis | |
| 8,226,654 B2 | 7/2012 | Ranck et al. | |
| 8,475,459 B2 | 7/2013 | Ellis | |
| 9,060,827 B2 | 6/2015 | Aledecoa | |
| 9,078,670 B2 | 7/2015 | Ellis | |
| 9,089,346 B2 | 7/2015 | Schoutens | |
| 9,333,564 B2 | 5/2016 | Santamarina et al. | |
| 9,603,610 B2 | 3/2017 | Richter et al. | |
| 2003/0018337 A1 | 1/2003 | Davis | |
| 2003/0187444 A1 * | 10/2003 | Overaker | A61B 17/0401 606/232 |
| 2011/0076640 A1 | 3/2011 | Jones | |
| 2012/0239042 A1 | 9/2012 | Lappin et al. | |
| 2013/0218160 A1 | 8/2013 | Bjorn et al. | |
| 2014/0276843 A1 | 9/2014 | Koay et al. | |
| 2016/0082525 A1 | 3/2016 | Gao | |

FOREIGN PATENT DOCUMENTS

| | | |
|---|---|---|
| EP | 1839611 A2 | 3/2007 |
| EP | 2722019 A1 | 4/2014 |
| GB | 2509739 A | 7/2014 |

OTHER PUBLICATIONS

GC Tech Europe Gmbh, Aadva "Choice of Aadva Implants", Apr. 6, 2017, 2 pgs.

* cited by examiner

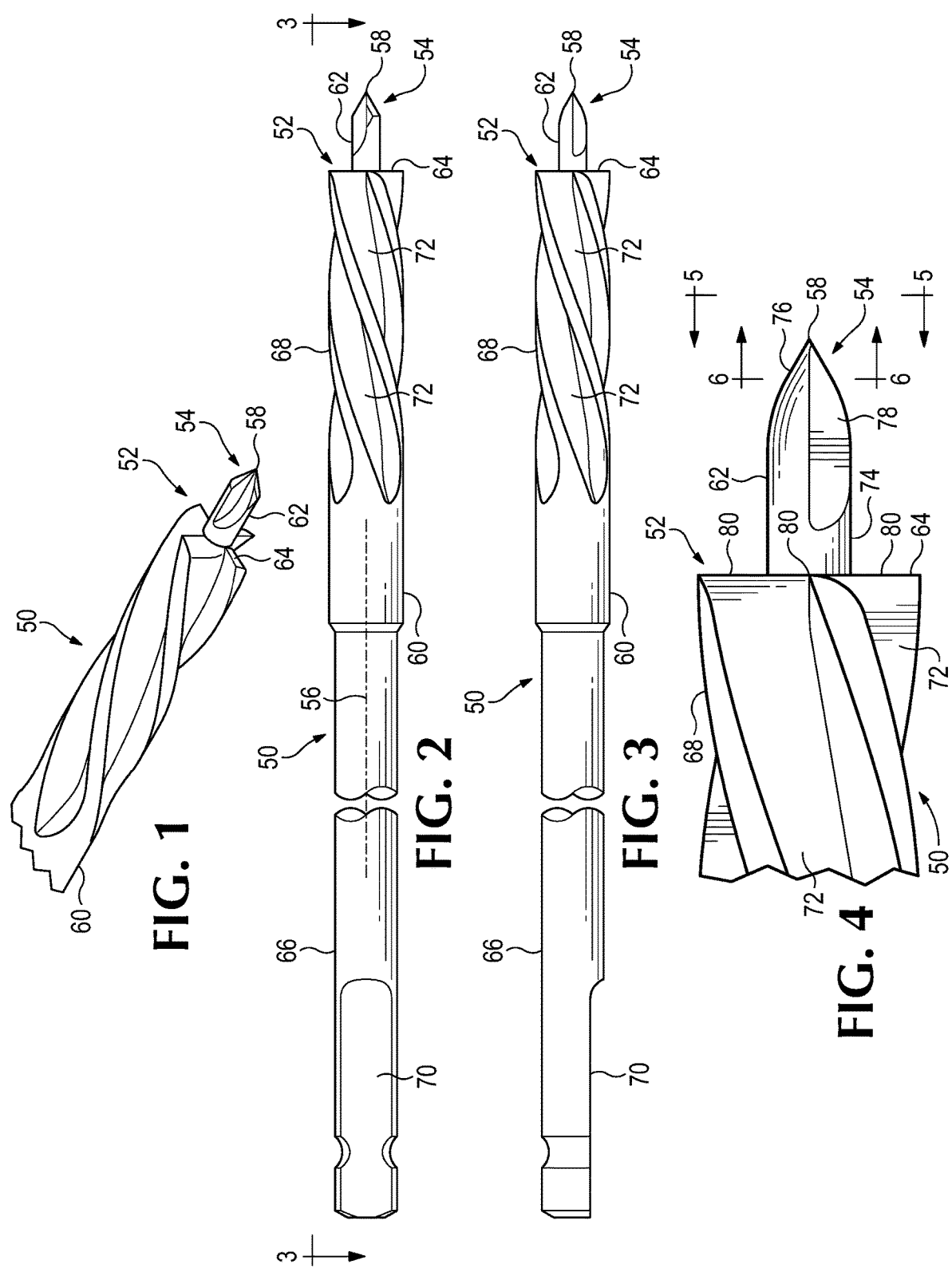

SYSTEM AND METHOD FOR INSTALLING A BICORTICAL IMPLANT IN BONE

The cortex is an outer shell surrounding spongy cancellous bone tissue and the medullary cavity of bones, and is formed of dense, hard cortical bone tissue. The mechanical properties of most bones, including their strength, stiffness, and ability to provide support and levers for movement, are determined primarily by the cortex.

Orthopedic fasteners, such as bone screws, may be designed for monocortical or bicortical installation. Monocortical fasteners enter and engage the cortex on only one side of the medullary cavity, and are generally too short to span the medullary cavity. Bicortical fasteners, in contrast, span the medullary cavity transversely and may engage both the near cortex and the far cortex on opposite sides of the medullary cavity. Bicortical engagement is often preferable because stress is distributed over a larger area and the fastener may be seated more stably.

A bone may be prepared to receive a bicortical implant, such as a fastener, by boring through the bone transversely to form a pair of coaxial holes in the near and far cortex of the bone. The holes can be bored to have the same diameter if the implant has a generally uniform diameter. However, the coaxial holes may need to be different in size (i.e., wider and narrower) to match the geometry of some bicortical implants. New approaches are needed for boring bone bicortically.

SUMMARY

The present disclosure provides orthopedic systems and methods for installing an implant and/or boring a bone bicortically. In an exemplary embodiment, the system may include a drill having a proximal boring portion configured to bore a larger hole in a bone more efficiently when the drill rotates in a first direction compared to an opposite second direction, and a distal boring portion configured to bore a smaller hole in the bone more efficiently when the drill rotates in the second direction. The system also may include an implant configured to be implanted at least partially in the bone, such that a first region of the implant is located in the larger hole and a second region of the implant is located in the smaller hole. In an exemplary method of boring bone, a larger hole and a smaller hole may be bored in a bone's near cortex and far cortex, respectively, by a shaft and a nose of a drill rotated in opposite directions.

BRIEF DESCRIPTION OF THE DRAWINGS

FIG. 1 is a fragmentary view of the leading portion of an orthopedic step drill having forward and reverse boring action provided by a shaft and a nose that respectively bore bone preferentially in opposite rotational directions of the drill about its long axis, in accordance with aspects of the present disclosure.

FIG. 2 is a broken side view of the drill of FIG. 1.

FIG. 3 is another broken side view of the drill of FIG. 1, taken generally along line 3-3 of FIG. 2.

FIG. 4 is a fragmentary side view of the drill of FIG. 1, taken as in FIG. 3 but showing only a leading section of the drill.

DETAILED DESCRIPTION

Figure 5:
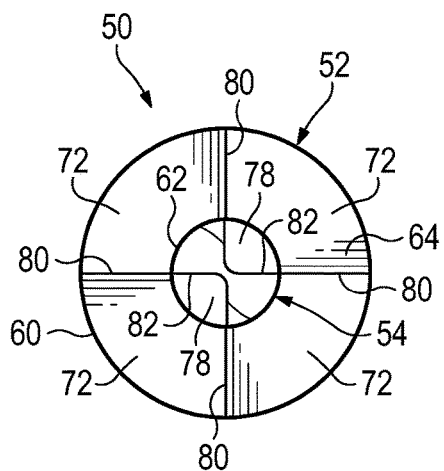
FIG. 5 is an end view of the drill of FIG. 1, taken generally along line 5-5 of FIG. 4.
Figure 6:
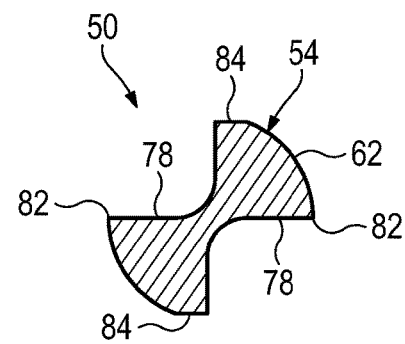
FIG. 6 is a sectional view of the drill of FIG. 1, taken generally along line 6-6 of FIG. 4.

The present disclosure provides orthopedic systems and methods for installing an implant and/or boring a bone bicortically. In an exemplary embodiment, the system may include a drill having a proximal boring portion configured to bore a larger hole in a bone more efficiently when the drill rotates in a first direction compared to an opposite second direction, and a distal boring portion configured to bore a smaller hole in the bone more efficiently when the drill rotates in the second direction. The system also may include an implant configured to be implanted at least partially in the bone, such that a first region of the implant is located in the larger hole and a second region of the implant is located in the smaller hole. In an exemplary method of boring bone, a larger hole and a smaller hole may be bored in a bone's near cortex and far cortex, respectively, by a shaft and a nose of a drill rotated in opposite directions.

The systems and methods of the present disclosure may offer various advantages for bicortical boring and/or bicortical implant installation. Forming coaxial holes of different size could be achieved by boring a bone with two drills of different diameter. First, a smaller drill may bore a pair of smaller coaxial holes through the near and far cortex of a bone. Second, a larger drill may enlarge only the coaxial hole in the near cortex. This approach can be slow, which undesirably increases the length of a surgical procedure, and alignment of the resulting holes may be imperfect. Alternatively, a standard step drill could be used to form holes of different size in a single pass. However, the surgeon may inadvertently advance the drill too far, causing the smaller hole in the far cortex also to be enlarged, which would render this hole unsuitable for effective engagement by the narrower leading portion of an implant. The present disclosure provides a drill, and a method of using the drill, to form holes of different size bicortically, without excessively complicating the boring procedure, and while reducing the risk of removing too much cortical tissue from the far cortex.

Further aspects of the present disclosure are described in the following sections: (I) step drill for boring bone bicortically, (II) implants, (III) methods of boring bone bicortically and installing an implant, and (IV) examples.

I. Step Drill for Boring Bone Bicortically

This section describes an exemplary step drill 50 to bore bone bicortically; see FIGS. 1-6. The drill interchangeably may be called a drill bit. The terms drilling, boring, and forming a hole(s) are synonyms in the present disclosure.

Drill 50 has a pair of boring portions 52, 54 configured to form respective bores of different diameter in spaced cortical regions of a bone. More specifically, proximal boring portion 52 is located more proximally along a long axis 56 of drill 50 and forms a larger hole (also called a wider hole), and distal boring portion 54 is located more distally and forms a smaller hole (also called a narrower hole). Boring portions 52, 54 may or may not be spaced from one another axially.

Each boring portion 52, 54 may have a preferential, rotational boring direction in which the boring portion cuts bone, and thus bores, more efficiently. The preferential boring directions for boring portions 52, 54 may be rotationally opposite one another. For example, in the depicted embodiment, proximal boring portion 52 preferentially bores when the drill is rotated counterclockwise (CCW), and distal boring portion 54 preferentially bores when the drill is rotated clockwise (CW). (The direction of rotation is defined when viewing the drill from its proximal end (i.e., the end that is closer to the user and/or a driver for the drill). In other embodiments, the preferential boring directions for boring portions 52, 54 may be switched, that is, CW and CCW, respectively. In still other embodiments, only the proximal boring portion may have a preferential direction of cutting/boring (e.g., see Example 1). Each boring portion may have any suitable relative boring efficiency for a preferential cutting direction, if any, compared to the opposite direction of rotation, such as at least 2, 3, 4, or 5 times the rate of advancement in cortical bone, among others, under the same amount of user-applied axial pressure.

One, neither, or both boring portions 52, 54 may have an outer diameter that tapers linear or nonlinearly toward a distal terminus of the boring portion (see FIGS. 2-4). In the depicted embodiment, distal boring portion 54 tapers to a point 58, and initially generates a conical recess in bone as the distal boring portion drills into the bone. Also, proximal boring portion 52 is non-tapered and initially generates a cylindrical recess and/or a planar surface region (also see Example 2). Advancement of the boring portions through respective spaced regions of the cortex of a bone may create cortical holes that are both cylindrical, while advancement of the distal (or proximal) boring portion into, but not completely through, the cortex may create an at least partially tapered hole in the cortex.

Drill 50 may have a shaft 60 that provides proximal boring portion 52, and a nose 62 that provides distal boring portion 54 and protrudes distally from shaft 60. The shaft may form a shoulder 64 at its leading end where proximal boring portion 52 is located. Shoulder 64 creates a transition from the larger diameter of shaft 60 to the smaller diameter of nose 62. The transition may be abrupt, as shown in the depicted embodiment, or more gradual (e.g., see Example 2). Accordingly, the shoulder may lie in a plane that is orthogonal to long axis 56, and/or may form any suitable average angle with an intersecting plane that is orthogonal to long axis 56, such as less than 10, 20, 30, or 40 degrees, among others.

Shaft 60 may have an elongated shank 66 and a fluted section 68 located distally therefrom. The shank may have a proximal tang 70 at which the drill can be attached to a suitable driver. The driver may be a power driver (e.g., powered electrically) or a manually-powered driver, among others. Fluted section 68 may define proximal boring portion 52 and one or more flutes 72 extending proximally therefrom. Each of the one or more flutes may be helical (as in the depicted embodiment), axial, or the like. If helical, the flutes may have left-handed helicity for an associated boring portion that bores preferentially in a counterclockwise direction (such as proximal boring portion 52 in the depicted embodiment), or may have right-handed helicity for an associated boring portion that bores preferentially in a clockwise direction. These relationships between flute helicity and preferential boring direction encourage bone swarf to be conveyed from an associated boring portion via the flutes as drilling is conducted. The fluted section may have "n" flutes that are rotationally offset from one another about long axis 56 by 360/n degrees.

Nose 62 may have a cylindrical region 74 and a tapered tip 76, with the cylindrical region located intermediate proximal boring portion 52 and tip 76. The nose may have one or more flutes 78, which may have any of the properties described above for fluted section 68 of shaft 60. In the depicted embodiment, flutes 78 are axial (also see Example 3).

Proximal boring portion 52 may be equipped with one or more cutting edges 80 (also called blades) (see FIGS. 4 and 5). For example, the proximal boring portion may have "c" cutting edges equally spaced from one another about long axis 56 by 360/c degrees. The depicted embodiment has four cutting edges, each lying in a plane orthogonal to long axis 56, but a different number of cutting edges, such as one, two, or three, among others, may be preferable in some embodiments. Each cutting edge may be located adjacent a respective flute 72. The cutting edge may be oriented and/or shaped to cut preferentially in one of the two opposite rotational directions of the drill about its long axis.

Distal boring portion 54 also may be equipped with one or more cutting edges 82 having any of the properties described above for the proximal boring portion (see FIGS. 5 and 6). The depicted embodiment has two cutting edges 82, but one, three, or four cutting edges, among others, may be preferable in some embodiments. Reliefs 84 may render nose 62 less efficient at boring when rotated opposite to its preferential boring direction.

Drill 50 may be cannulated for placement over a guide wire. Alternatively, the drill may not be cannulated.

Further aspects of exemplary drills for the systems and methods of the present disclosure are described below in Sections III and IV.

II. Implants

This section describes exemplary implants for installation in a coaxial pair of cortical holes formed by any of the step drills of the present disclosure; see FIGS. 7-16.

An implant for installation in a pair of cortical holes bored as disclosed herein may have any suitable structure. The implant is biocompatible, and may be linear or nonlinear, and may be rigid or flexible. The implant may be described as a bicortical implant, which is any implant that spans a coaxial pair of cortical holes, either inside or outside the bone, or both inside and outside. The implant has respective regions located in the holes, and may fit loosely or tightly into each hole. Accordingly, each hole may or may not be completely filled with a region of the implant. Exemplary implants include fasteners, bushings, and the like. Accordingly, the implant may include a screw, wire, cable, suture, anchor, or a combination thereof, among others.

Figure 7:
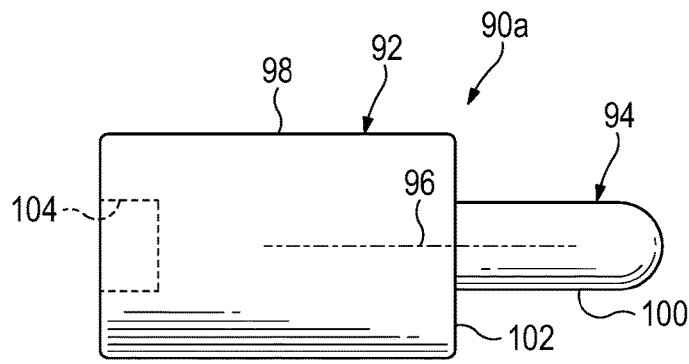
FIG. 7 is a side view of an exemplary bicortical implant that may be installed in a bone bored bicortically by the drill of FIG. 1, in accordance with aspects of the present disclosure.

FIG. 7 shows an exemplary implant 90a that is configured to be placed transversely into a long bone. Implant 90a has a trailing region 92 and a leading region 94 arranged coaxially with one another on a long axis 96. The trailing and leading regions having different diameters from one another, such that the trailing region is wider than the leading region. More specifically, trailing region 92 has a diameter that matches a diameter of the larger hole bored by proximal boring portion 52 of drill 50, and leading region 94 has a diameter matching a diameter of the smaller hole bored by distal boring portion 54 of drill 50 (see Section I). The diameter of trailing region 92 and/or leading region 94 that matches a cortical hole diameter may be a major diameter or a minor diameter. Each region 92, 94 may or may not be cylindrical.

Trailing region 92 may form a body 98 of the implant, and leading region 94 may form a post 100. The trailing region may form a shoulder 102 at its distal end, from which leading region 94 (such as post 100) may protrude. A driver interface 104 may be formed at the proximal end of trailing region 92, to facilitate driving the implant into bone (e.g., by application of torque and/or axial force) with a suitable driver.

Figure 8:
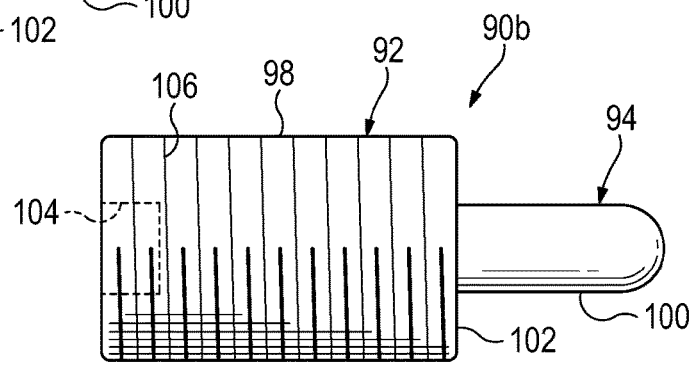
FIG. 8 is a side view of another exemplary bicortical implant that may be installed in a bone bored bicortically by the drill of FIG. 1, in accordance with aspects of the present disclosure.
Figure 9:
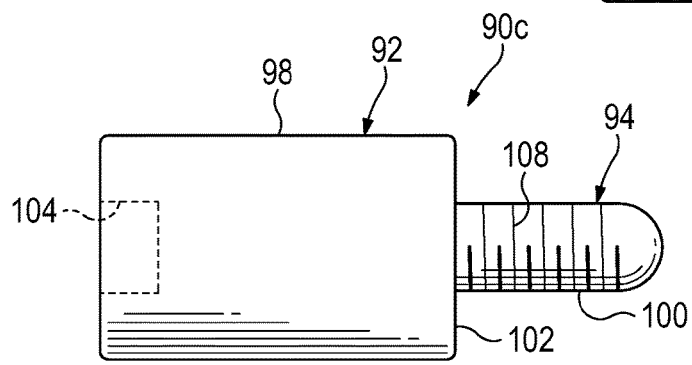
FIG. 9 is a side view of still another exemplary bicortical implant that may be installed in a bone bored bicortically by the drill of FIG. 1, in accordance with aspects of the present disclosure.
Figure 10:
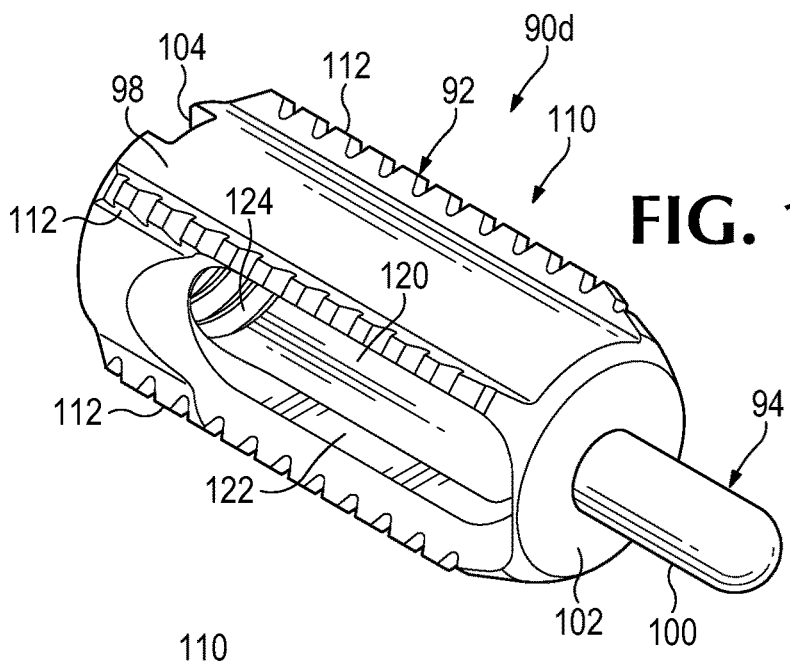
FIG. 10 is an isometric view of yet another exemplary bicortical implant that may be installed in a bone bored bicortically by the drill of FIG. 1, with the implant being structured as a bushing for an intramedullary nail, in accordance with aspects of the present disclosure.

FIGS. 8 and 9 show implants 90b, 90c that are similar to the implant of FIG. 7, except having an external thread 106 or 108 to attach the implant to bone at one of the cortical holes formed by drill 50. In some embodiments, trailing and leading regions 92, 94 each may have a respective external thread 106 or 108, formed radially outward of body 98 or post 100, respectively. Accordingly, these implants may be driven into bone rotationally. More generally, the implants disclosed herein may have one or more external protrusions provided by region 92 or 94 of FIG. 8, or regions 92 and 94 of FIG. 9, to provide attachment to bone.

FIGS. 10-14 show an implant 90d structured as a bushing 110. The bushing has a general structure similar to implant 90b of FIG. 8, namely, a cylindrical body 98 and a post 100 projecting from a shoulder 102 formed at a leading end of the body. Also, bushing 110 has a plurality of external protrusions 112 formed on body 98 and arranged to function as an external thread, or to otherwise restrict removal of the implant from bone.

Figure 11:
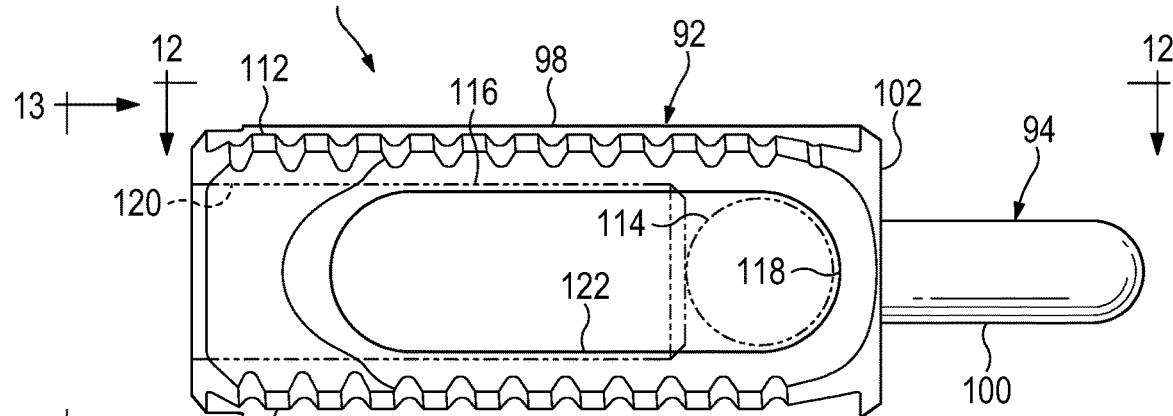
FIG. 11 is a side view of the bushing of FIG. 10.

Body 98 may be hollow, defining an internal void to allow the body to receive an intramedullary nail 114 transversely and a set screw 116 axially (see FIG. 11). The set screw is adjustable to clamp a section of the nail, when positioned inside the body, between a leading end of the set screw and an internal wall 118 of the bushing. The internal void of the body may include an aperture 120 that extends into the body axially from its trailing end, and an opening 122 that intersects the aperture and passes through the body transversely (e.g., orthogonally, such as diametrically, to the aperture). Aperture 120 may be sized to receive set screw 116, and may define an internal thread 124 that is complementary to an external thread of the set screw. Opening 122 may be sized to allow a leading end of nail 114 to pass through body 98 transversely, such that the nail extends through the opening.

Figure 12:
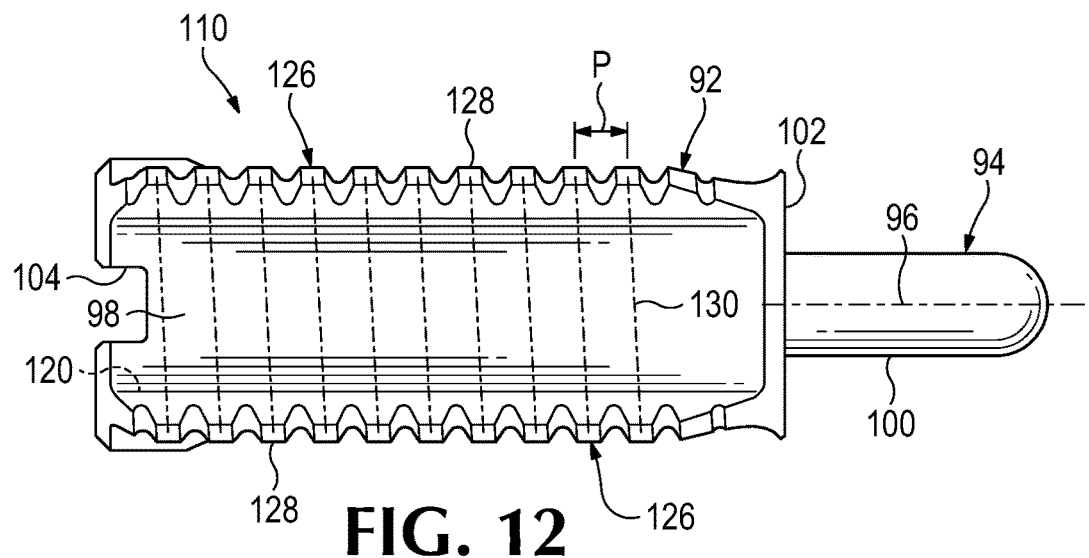
FIG. 12 is another side view of the bushing of FIG. 10, taken generally along line 12-12 of FIG. 11.
Figure 13:
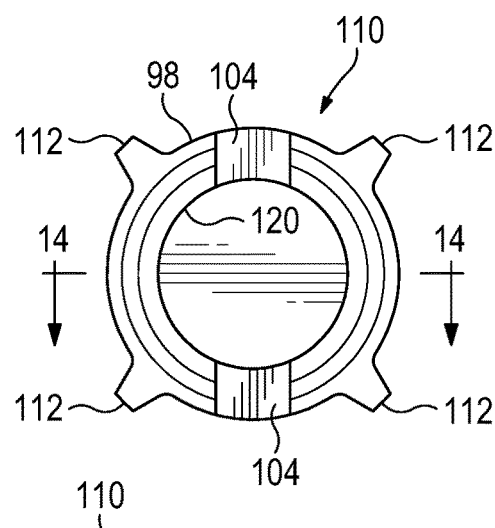
FIG. 13 is an end view of the bushing of FIG. 10, taken generally along line 13-13 of FIG. 11.
Figure 14:
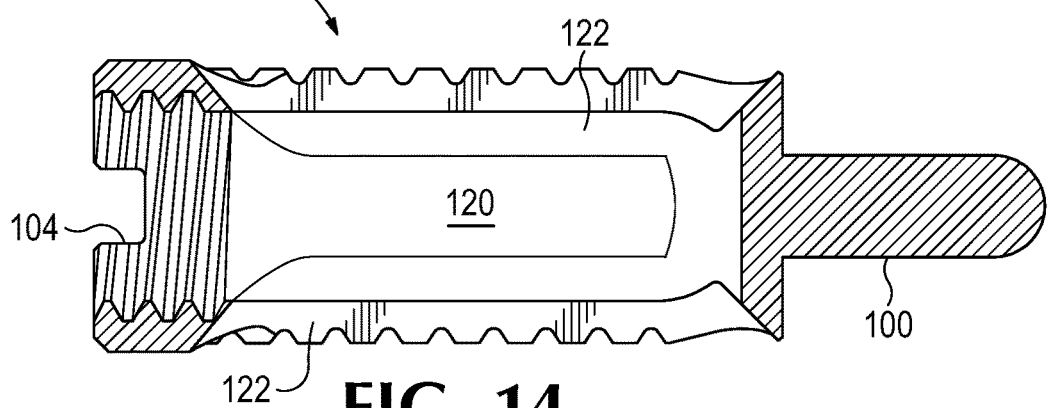
FIG. 14 is a sectional view of the bushing of FIG. 10, taken generally along line 14-14 of FIG. 13.

External protrusions 112 may form rows 126 of teeth 128 (see FIG. 12). Each row 126 may be arranged parallel to long axis 96, and the teeth may be uniformly spaced within each row. The teeth of all the rows considered collectively may be arranged on the same helical path 130. The pitch (p) of the helical path (i.e., the distance between successive full turns of the path) may be equal to the spacing of adjacent teeth within each row. The rows of teeth may be axially offset from one another by a fraction of the pitch to place all the teeth on the helical path. For example, with n uniformly spaced rows of teeth, the rows may be successively offset from one another by a distance of p/n. In other embodiments, the teeth may be replaced by a more complete external thread.

Figure 15:
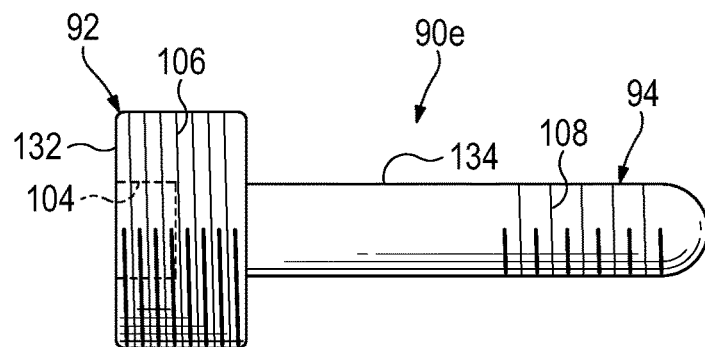
FIG. 15 is a side view of still yet another exemplary bicortical implant that may be installed in a bone bored bicortically by the drill of FIG. 1, in accordance with aspects of the present disclosure.

FIG. 15 shows another exemplary implant 90e that may be installed bicortically. Compared to the implants of FIGS. 7-9, implant 90e has a shorter trailing region 92 and a longer leading region 94, to form a head 132 and a shaft 134, respectively. Head 132 and/or shaft 134 may be externally threaded. For example, in the depicted embodiment, the head and shaft have respective external threads 106, 108 of different pitch. In other examples, the trailing and leading regions of the implant may have respective external threads of the same pitch as one another.

Figure 16:
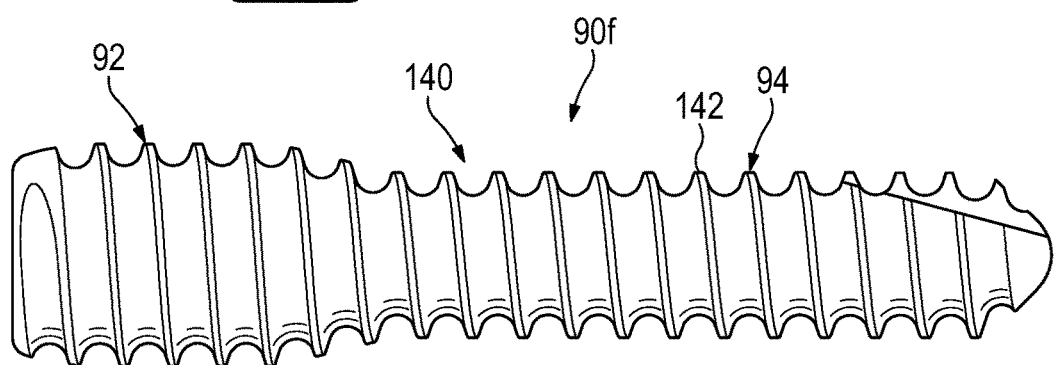
FIG. 16 is a side view of yet still another exemplary bicortical implant, a screw, that may be installed in a bone bored bicortically by a step drill constructed as FIG. 1 except with different relative diameters of the shaft and nose of the drill, in accordance with aspects of the present disclosure.

FIG. 16 shows yet another exemplary implant 90f that may be installed bicortically. Implant 90f is structured as a "headless" bone screw 140 having a leading region 92 and a trailing region 94 of different diameter from one another. An external thread 142 may be formed on both regions 92, 94. The difference in diameter between trailing and leading regions 92, 94 may be less than for implants 90a-90e, making the transition between these regions more gradual and a corresponding shoulder much less pronounced.

The implants (and drills) disclosed herein may have any suitable composition. Each may be formed of any suitable biocompatible material(s) and/or bioresorbable (bioabsorbable) material(s). Illustrative biocompatible materials that may be suitable include (1) metal (for example, titanium or titanium alloy, cobalt-chrome alloy, stainless steel, magnesium or magnesium alloy (e.g., an alloy including magnesium, calcium, and zinc) etc.); (2) polymer/plastic (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) bioresorbable material or polymer/plastic (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, poly(hydroxyalkanoate)s of the PHB-PHV class, other bioresorbable polyesters, and/or natural polymers (such as collagen or other polypeptides, polysaccharides (e.g., starch, cellulose, and/or chitosan), any copolymers thereof, etc.)); or (4) any combination thereof. In exemplary embodiments, the implant is formed of metal or polymer, and the drill is formed of metal.

III. Methods of Boring Bone Bicortically and Installing An Implant

This section describes exemplary methods of installing an implant in a bone 150 by boring the bone bicortically with step drill 50 (also see Section I) and then placing the implant into the bored bone; see FIGS. 17-25. The method steps described in this section may be performed in any suitable order and combination using any of the drills and implants of the present disclosure.

FIGS. 17-24 illustrate configurations produced by performing a method of installing implant 90d (see FIGS. 10-14) that includes boring coaxial holes in a bone with drill 50 and placing the implant into the holes. The sequence of boring directions (CW, CCW, CW) utilized with drill 50 may be changed to a different sequence (e.g., (CCW, CW, CCW), (CW, CCW), or (CCW, CW)) for other drill embodiments (also see Example 1).

The first boring direction may be CW or CCW. Clockwise is the conventional "forward" direction for drilling. Accordingly, the drill may be designed such that the first boring direction is CW for convenience to the practitioner, for example, by avoiding the need to set the driver of the drill to "reverse" at the start of the drilling procedure. Alternatively, the drill may be designed such that the first boring direction is CCW, to help remind the practitioner that the drilling procedure will require switching the direction of boring one or more times.

Bone 150 is shown in fragmentary and schematic form, with only cortex 152 being present. A medullary cavity 154 (and/or cancellous bone) may be located radially inward of cortex, and may contain marrow and/or may have been reamed. The bone may (or may not) be a long bone, and boring may be performed in the shaft of the bone or closer to an end of the bone. Cavity 154, contents therein, and/or cancellous bone generally do not provide significant resistance to advancement of drill 50 compared to cortical bone of cortex 152. Transversely-spaced regions of cortex 152 that are respectively closer and farther from the site of entry of drill 50 into bone 150, and separated by medullary cavity 154, are described as the near cortex 156 and the far cortex 158.

Figure 17:
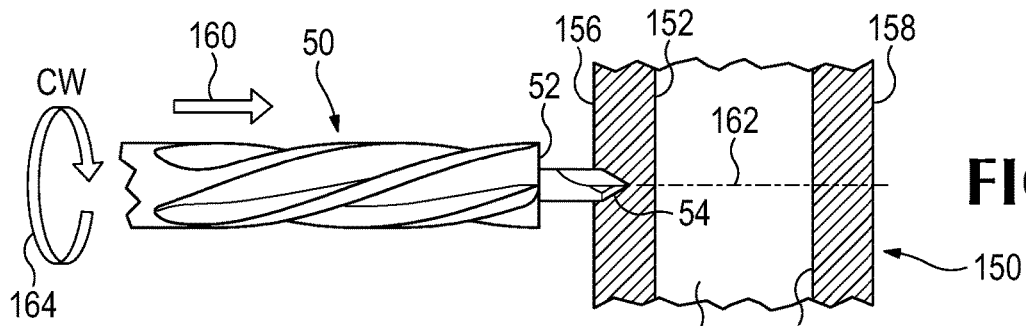
FIGS. 17-24 are fragmentary, sectional views of a bone, and particularly the near cortex, far cortex, and medullary cavity thereof, illustrating performance of exemplary methods of boring bone bicortically and installing a bicortical implant, using the step drill of FIG. 1 and the bicortical implant of FIG. 10, in accordance with aspects of the present disclosure.

FIG. 17 shows distal boring portion 54 being advanced axially, indicated by an arrow at 160, into near cortex 156 along a drilling axis 162. Drill 50 is being rotated in the preferential boring direction for the distal boring portion (but not proximal boring portion 52), which for the depicted embodiment is clockwise (CW). This configuration may be generated during Phase I of drilling.

Figure 18:
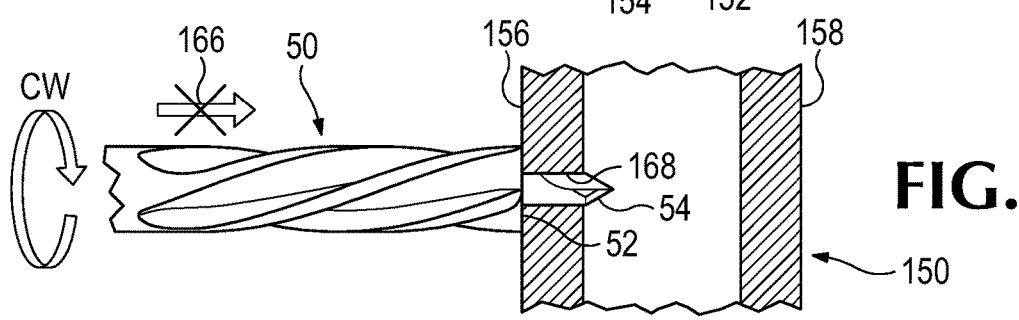

FIG. 18 shows the end of Phase I, with axial advancement of drill 50 being impeded, indicated at 166, when proximal boring portion 52 reaches near cortex 156, while drill 50 is still being rotated in the preferential boring direction for distal boring portion 54. Proximal boring portion 52 is being rotated in its less efficient boring direction, and thus enters the near cortex relatively slowly, if at all. The practitioner (e.g., a surgeon) can rely on visual and/or haptic feedback to detect when the end of Phase I has been reached and clockwise drilling should be stopped, and the direction of drill rotation reversed to counterclockwise, to start Phase II of drilling. At the end of Phase I, distal boring portion 54 has formed a smaller through-hole 168 (or blind hole) in near cortex 156, and may (or may not) have passed completely through the near cortex.

Figure 19:
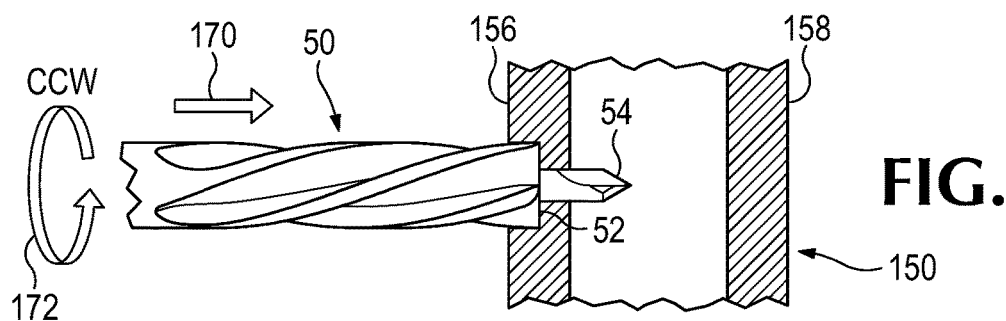

FIG. 19 shows proximal boring portion 52 being advanced axially, indicated by an arrow at 170, into near cortex 156 during Phase II of drilling, while drill 50 is being rotated in the opposite direction (CCW) from Phase I, indicated at 172. Counterclockwise is the preferential boring direction for proximal boring portion 52 in the depicted embodiment, and thus the drill may advance relatively more rapidly.

Figure 20:
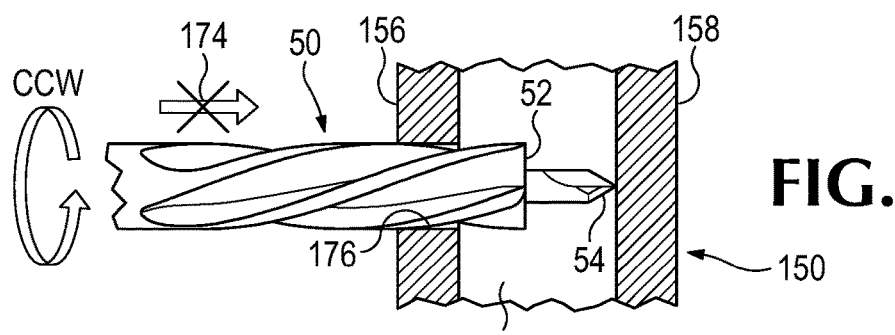

FIG. 20 shows the end of Phase II, with axial advancement of drill 50 being impeded, indicated at 174, once distal boring portion 54 engages far cortex 158. Distal boring portion 54 is being rotated in its less efficient boring direction (CCW), and thus enters the far cortex relatively slowly, if at all. Accordingly, the practitioner can rely on haptic feedback (interchangeably called "feel") to detect when the end of Phase II has been reached and boring with proximal boring portion 52 should be stopped. The direction of drill rotation then is reversed, to CW in the depicted embodiment, to start Phase III of drilling. At the end of Phase II, proximal boring portion 52 may have formed a larger hole 176 in and/or through near cortex 156. In some embodiments, the practitioner may reverse the direction of drilling at any time after proximal boring portion 52 has passed through near cortex 156 and entered medullary canal 154, and before the proximal boring portion has reached far cortex 158. For example, the practitioner may utilize haptic feedback to detect when proximal boring portion 52 has passed through near cortex 156, as a drop in axial and/or rotational resistance to advancement of the drill.

Figure 21:
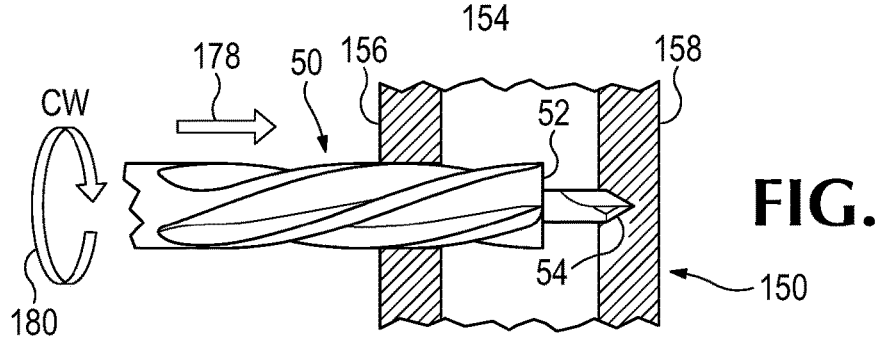

FIG. 21 shows distal boring portion 54 being advanced, indicated by an arrow at 178, into far cortex 158 during Phase III of drilling, while drill 50 is being rotated CW, indicated at 180. Clockwise is the preferential boring direction for distal boring portion 54, and thus the drill may advance relatively rapidly.

Figure 22:
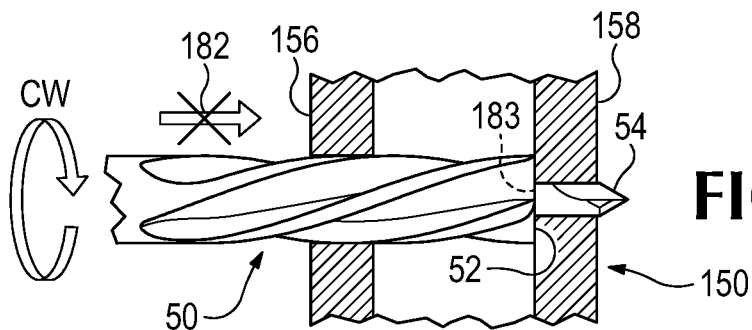

FIG. 22 shows the end of Phase III, with advancement of drill 50 being impeded, indicated at 182, when proximal boring portion 52 reaches far cortex 158, while drill 50 is still being rotated CW. Proximal boring portion 52 is being rotated in its less efficient boring direction, and thus enters the far cortex relatively slowly (e.g., by grinding action), if at all. Accordingly, proximal boring portion 52 may form a milled recess 183 on the inside surface of the far cortex. The recess may be cylindrical, with a planar floor, or may have a different shape determined by the structure of proximal boring portion 52 (e.g., see Example 2).

Figure 23:
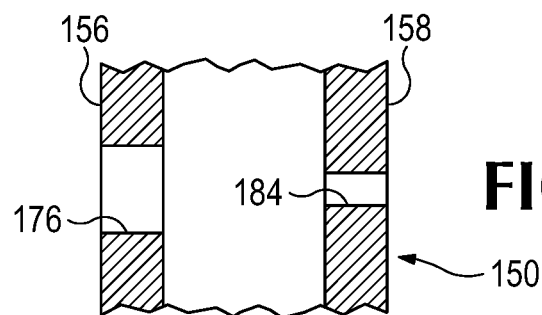

The practitioner can rely on haptic feedback to assess when the end of Phase III has been reached, and the drill should be removed from bone 150 (see FIG. 23). At the end of Phase III, distal boring portion 54 has formed a smaller hole 184 in and/or through far cortex 158, and in coaxial alignment with larger hole 176 through near cortex 156.

Figure 24:
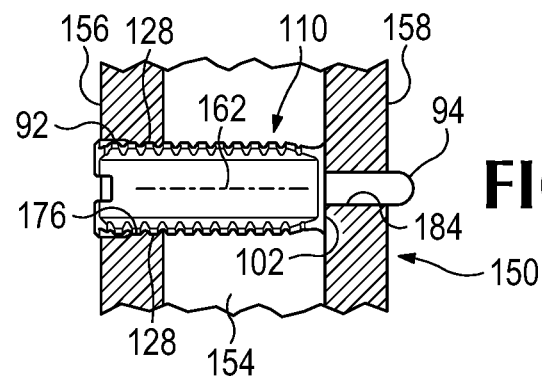

FIG. 24 shows an implant, bushing 110, operatively installed in bone 150. The implant may be driven into the bone on drilling axis 162, by application of torque and/or axial force to the implant, such that the implant is partially located in each hole 176, 184, and spans medullary cavity 154. More specifically, trailing region 92 may be located at least partially in wider hole 176, and leading region 94 may be located at least partially in narrower hole 184. Shoulder 102 may be abutted with the inner side of far cortex 158, and optionally a milled surface region thereof. One or more external protrusions (e.g., teeth 128, barbs, fins, an external thread, etc.) of the implant may be engaged with cortical bone bounding one or both holes 176, 184, to resist removal of the implant, and/or the implant may be press-fitted into one or both holes to resist removal. One or both ends of the implant may protrude from bone 150, or either or both ends may be flush or recessed with respect to the exterior of the bone.

Figure 25:
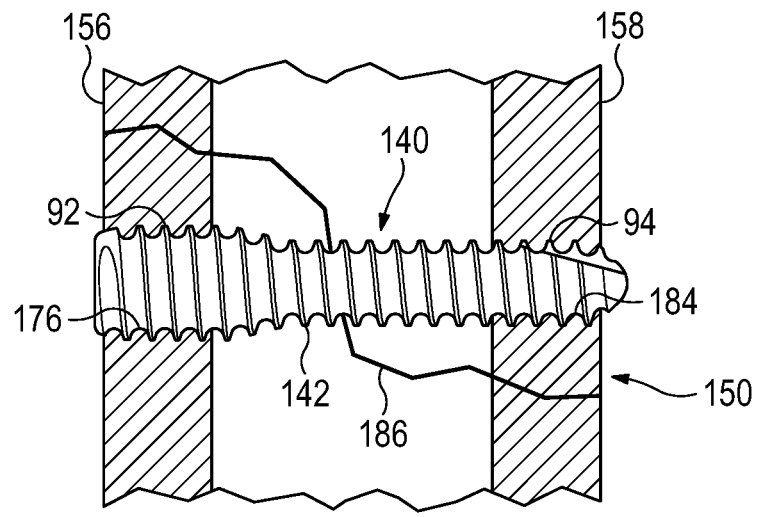
FIG. 25 is a fragmentary, sectional view of a fractured bone, and particularly the near cortex, far cortex, and medullary cavity thereof, taken after installation of the screw of FIG. 16 in cortical bores created by a corresponding embodiment of the step drill of FIG. 1, to further exemplify methods of the present disclosure.
Figure 26:
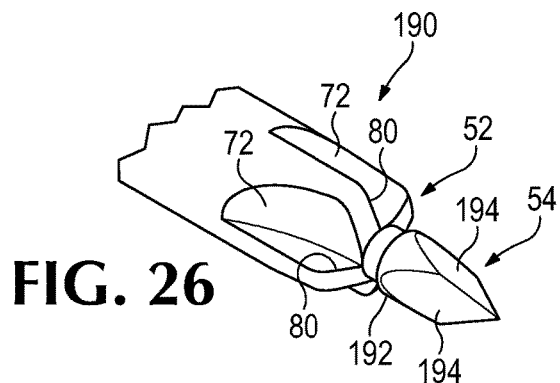
FIG. 26 is a fragmentary, isometric view of the leading portion of an exemplary orthopedic step drill having a shaft that bores preferentially in one rotational direction of the drill and a trocar nose that bores non-preferentially in both rotational directions of the drill, in accordance with aspects of the present disclosure.
Figure 27:
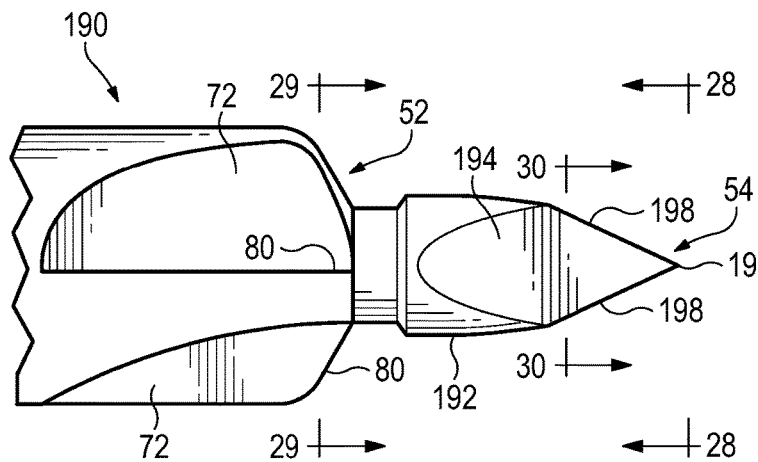
FIG. 27 is a fragmentary side view of the step drill of FIG. 26.
Figure 28:
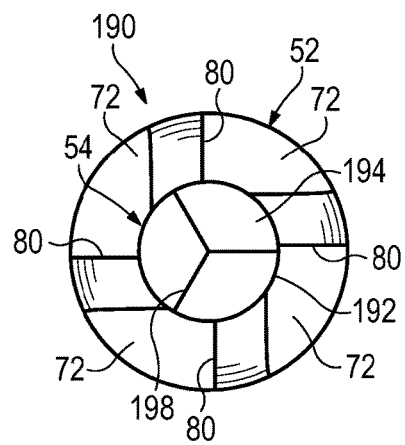
FIG. 28 is an end view of the step drill of FIG. 26, taken generally along line 28-28 of FIG. 27.
Figure 29:
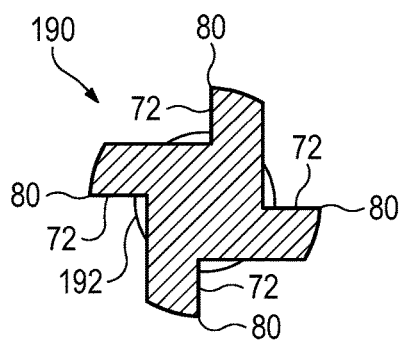
FIG. 29 is a sectional view of the step drill of FIG. 26, taken generally along line 29-29 of FIG. 27.
Figure 30:
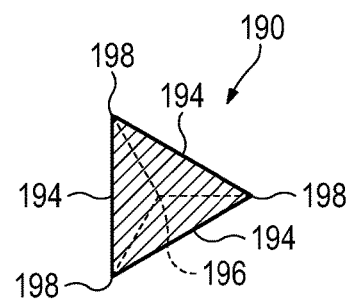
FIG. 30 is a sectional view of the step drill of FIG. 26, taken generally along line 30-30 of FIG. 27.

FIG. 25 shows bone 150 fixed with a different implant, bone screw 140. Holes 176, 184 of suitable diameter have been bored in near cortex 156 and far cortex 158, respectively, with a suitably dimensioned embodiment of drill 50, using the drilling procedure described above. Screw 140 has been placed into the holes, such that external thread 142 attaches the implant to bone at each of holes 176, 184. The implant may be self-tapping, to form complementary internal threads in the bone at the holes as the implant is driven into the bone. Bone 150 may have a fracture 186 (such as an oblique fracture) that is spanned by the implant (or any other implant disclosed herein). In other embodiments, bone screw 140 may extend through an aperture of an intramedullary nail, and, optionally, may lock to the nail by threaded engagement therewith.

IV. EXAMPLES

The following examples describe selected aspects and embodiments of the present disclosure related to a step drill, systems including a step drill and a corresponding bicortical implant, and methods of boring bone bicortically and/or installing a bicortical implant. The aspects and features of the systems and methods described in each of these examples may be combined with one another and with aspects and features of the systems, devices, and methods described elsewhere in the present disclosure, in any suitable combination. These examples are intended for illustration and should not limit the entire scope of the present disclosure.

Example 1

Step Drill with Trocar Nose

This example describes an exemplary step drill 190 having a trocar nose 192, and methods of using the drill to install a bicortical implant; see FIGS. 26-30.

Drill 190 may have any combination of the features described above in Section I for drill 50 (also see FIGS. 1-6). For example, the drill may have a proximal boring portion 52 and a distal boring portion 54. Proximal boring portion 52 may have a preferential boring direction, namely, counterclockwise as in the depicted embodiment or clockwise. The preferential boring direction may be created by cutting edges 80, which may border flutes 72.

Distal boring portion 54 may be structurally different from that of drill 50, and may bore with similar efficiency in both rotational directions of the drill. For example, the distal boring portion may include a plurality of facets 194 (e.g., three in the depicted embodiment) that meet one another to create a pointed tip 196 and a plurality of cutting edges 198.

Drill 190 may be used to form respective holes of different diameter with boring portions 52, 54, generally as described above for drill 50 (see Section III). However, since distal boring portion 54 bores in either direction, the practitioner may perform Phases I and II of the drilling procedure with the drill rotating in the same direction, namely, the preferred boring direction for proximal boring portion 52. Phase II of the drilling procedure may be ended when the practitioner feels a drop in resistance to drill advancement, indicating that proximal boring portion 52 has bored completely through the near cortex and has entered the medullary cavity. Accordingly, the practitioner may bore through the near cortex successively with both boring portions of the drill, while the drill is rotated in the preferred boring direction of the proximal boring portion. The practitioner then may reverse the direction of rotation of the drill, and continue with Phase III, as described above for drill 50. Therefore, the practitioner may reverse rotation of drill 190 only once, when haptic feedback indicates that proximal boring portion 52 has entered the medullary cavity.

Example 2

Drill and Implant with Convex Shoulders

Figure 31:
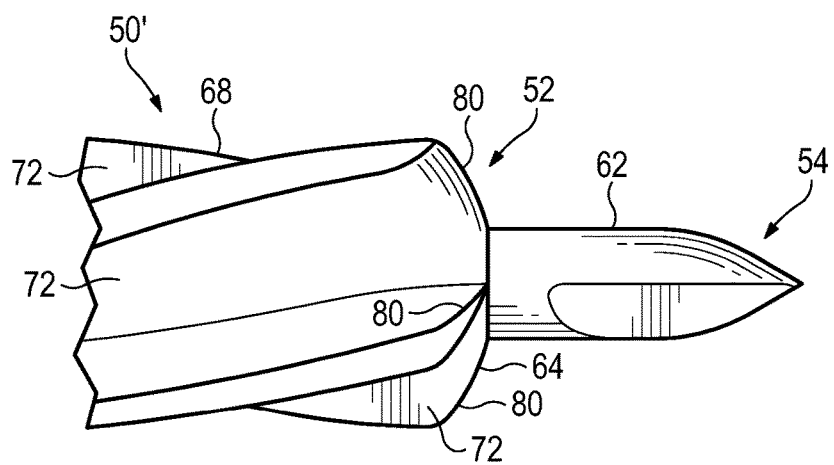
FIG. 31 is a fragmentary side view of a leading portion of an exemplary step drill having a rounded boring portion formed at the leading end of the drill's shaft, in accordance with aspects of the present disclosure.
Figure 32:
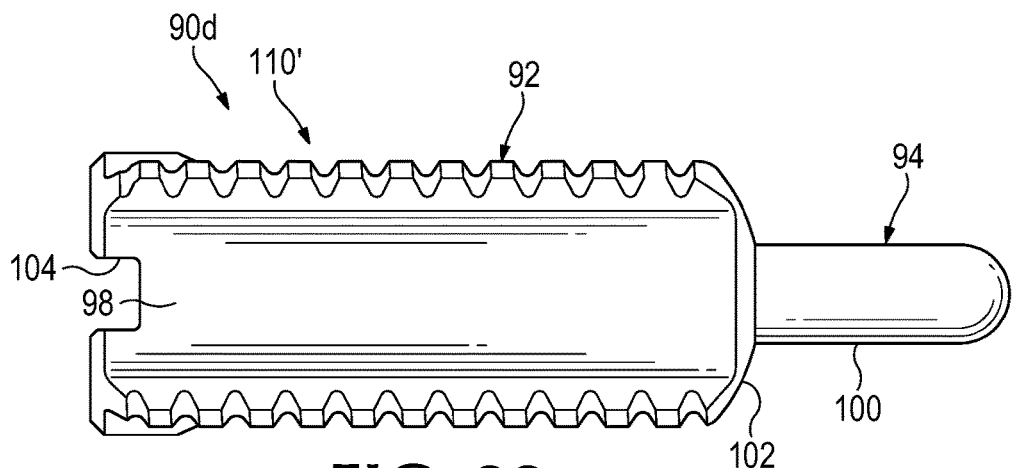
FIG. 32 is a side view of an alternative embodiment of the bicortical implant of FIG. 10, in which the implant has a rounded shoulder corresponding to the rounded boring portion of the drill of FIG. 31, in accordance with aspects of the present disclosure.

This example describes an exemplary step drill 50' and a corresponding implant 90d, bushing 110', each having a convex shoulder (64 and 102, respectively); see FIGS. 31 and 32.

Step drill 50' is similar to step drill 50 described above in Section I (see FIGS. 1-6) but has a tapered proximal boring portion 52. More specifically, in drill 50', proximal boring portion 52, shoulder 64, and each cutting edge 80 have a convex curvature (or, alternatively, a linear taper) when projected orthogonally onto a plane parallel to the long axis of the drill. The convex curvature of proximal boring portion 52 may be configured to generally match the concave curvature of the inner side of the far cortex where the drill will be used. This geometry of drill 50' can reduce the risk of proximal boring portion 52 undesirably milling the far cortex excessively, near the end of Phase III (also see FIG. 22). For comparison, proximal boring portion 52 of drill 50 mills the inner side of the far cortex less evenly, which may make it more difficult for the practitioner to detect the end of Phase III. When drill 50 has reached the configuration of FIG. 22, milling action by proximal boring portion 52 may have removed excessive amounts of cortical bone from the far cortex, even potentially breaching the far cortex.

Bushing 110' is similar to bushing 110 described above in Section II (see FIGS. 10-14), except that bushing 110' has a convex shoulder 102, while that of bushing 110 is planar. The convex shoulder may have a taper (and/or a curvature) configured to generally match the concave curvature of the inner side of the far cortex and matching that of proximal boring portion 52 of drill 50'. Accordingly, shoulder 102 will be complementary to a recess, if any, formed in the inside surface of the far cortex by the milling action of proximal boring portion 52 of drill 50'.

Example 3

Drill Nose with Serrated Cutting Edge

Figure 33:
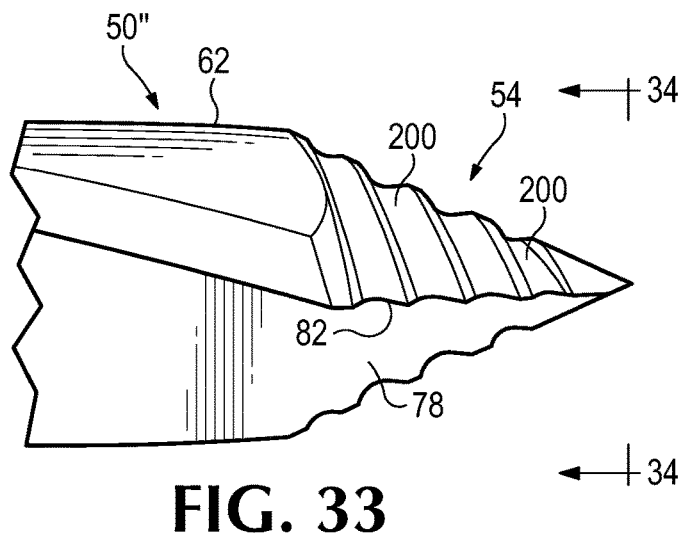
FIG. 33 is a fragmentary side view of another exemplary orthopedic step drill for boring bone bicortically, taken around the nose of the drill, in accordance with aspects of the present disclosure.
Figure 34:
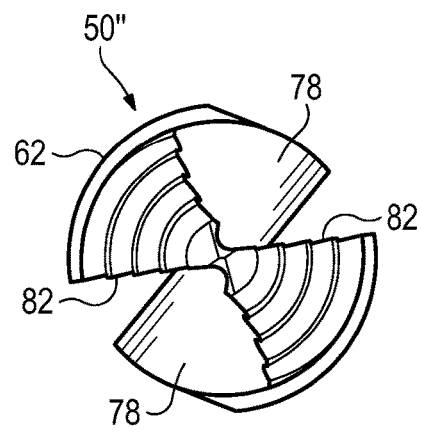
FIG. 34 is an end view of the nose of the drill of FIG. 33.

This example describes a step drill 50" having a distal boring portion 54 formed by a nose 62 and including serrated cutting edges 82; see FIGS. 33 and 34. The nose of drill 50" may be incorporated into any of the drills of the present disclosure.

Distal boring portion 54 is created by a conical section having one or more helical furrows 200 formed therein. A pair of helical flutes 78 defined by nose 62 and bordering cutting edges 82 extend to positions near the distal boundary of the conical section.

Example 4

Selected Embodiments

This example describes selected embodiments of the present disclosure as a series of numbered paragraphs.

Paragraph 1. An orthopedic system, comprising: (A) a drill including a proximal boring portion and a distal boring portion, the proximal boring portion being configured to bore a larger hole in a bone more efficiently when the drill rotates in a first direction compared to an opposite second direction, the distal boring portion being configured to bore a smaller hole in the bone more efficiently when the drill rotates in the second direction compared to the first direction; and (B) an implant configured to be implanted at least partially in the bone, such that a first region of the implant is located in the larger hole and a second region of the implant is located in the smaller hole.

Paragraph 2. The orthopedic system of paragraph 1, wherein the implant has a trailing region with a diameter corresponding to the larger hole and a leading region with a diameter corresponding to the smaller hole.

Paragraph 3. The orthopedic system of paragraph 2, wherein at least one of the trailing region and the leading region of the implant has one more external protrusions configured to resist removal of the implant from the bone.

Paragraph 4. The orthopedic system of paragraph 2 or 3, wherein at least one of the trailing region and the leading region of the implant has an external thread or protrusions configured to function as an external thread.

Paragraph 5. The orthopedic system of any one of paragraphs 1-4, wherein the implant is configured to be driven into bone by rotation.

Paragraph 6. The orthopedic system of any one of paragraphs 3-5, wherein the implant has a radially inner portion from which the one or more external protrusions project, and wherein the inner portion defines the diameter corresponding to that of the larger hole and/or the diameter corresponding to that of the smaller hole.

Paragraph 7. The orthopedic system of any one of paragraphs 1-6, wherein the implant includes a screw.

Paragraph 8. The orthopedic system of any one of paragraphs 1-7, wherein the implant is linear.

Paragraph 9. The orthopedic system of any one of paragraphs 1-7, wherein the implant includes a suture, a wire, a cable, or a combination thereof.

Paragraph 10. The orthopedic system of any one of paragraphs 1-9, wherein the proximal boring portion of the drill is configured to bore the larger hole more efficiently when the drill is rotating counterclockwise, and wherein the distal boring portion of the drill is configured to bore the smaller hole more efficiently when the drill is rotating clockwise.

Paragraph 11. The orthopedic system of any one of paragraphs 1-9, wherein the proximal boring portion of the drill is configured to bore the larger hole more efficiently when the drill is rotating clockwise, and wherein the distal boring portion of the drill is configured to bore the smaller hole more efficiently when the drill is rotating counterclockwise.

Paragraph 12. The orthopedic system of any one of paragraphs 1-11, wherein the drill includes a nose projecting from a shaft, wherein a leading section of the shaft provides the proximal boring portion, and wherein a leading section of the nose provides the distal boring portion.

Paragraph 13. The orthopedic system of any one of paragraphs 1-12, wherein the proximal boring portion and/or the distal boring portion has a plurality of cutting edges that are rotationally offset from one another about a long axis of the drill.

Paragraph 14. The orthopedic system of any one of paragraphs 1-13, wherein the proximal boring portion tapers toward the distal boring portion.

Paragraph 15. The orthopedic system of any one of paragraphs 1-14, wherein the implant includes a shoulder at a junction between the leading region and the trailing region, wherein the proximal boring portion is configured to form a recess in an inner side of a far cortex of the bone, and wherein the recess is complementary to the shoulder.

Paragraph 16. A method of installing an implant, the method comprising: (A) selecting a drill having a nose protruding from a shaft, the shaft being configured to bore more efficiently when the drill rotates in a first direction compared to an opposite second direction; (B) drilling into a bone with the nose of the drill at a near cortex of the bone; (C) boring through the near cortex with the shaft of the drill to form a larger hole in the near cortex as the drill is rotated in the first direction; (D) forming a smaller hole in a far cortex of the bone with the nose of the drill as the drill is rotated in the opposite second direction; and (E) placing the implant at least partially in the bone such that respective regions of the implant are located in the larger hole and the smaller hole.

Paragraph 17. The method of paragraph 16, wherein the step of forming a smaller hole includes a step of advancing the drill along an axis until contact between a leading end of the shaft and the far cortex is detected.

Paragraph 18. The method of paragraph 16 or 17, wherein the step of forming a smaller hole includes a step of boring a smaller hole through the far cortex.

Paragraph 19. The method of any one of paragraphs 16-18, wherein the nose is configured to bore more efficiently when the drill rotates in the second direction compared to the first direction, and wherein the step of drilling is performed while the drill is rotating in the second direction.

Paragraph 20. The method of any one of paragraphs 16-19, further comprising a step of reversing rotation of the drill from the second direction to the first direction when the shaft of the drill closely approaches or contacts the near cortex.

Paragraph 21. The method of any one of paragraphs 16-20, wherein the shaft includes a proximal boring portion that bores the larger hole, further comprising a step of reversing rotation of the drill from the first direction to the second direction after the proximal boring portion has passed through the near cortex and before the proximal boring portion contacts the far cortex.

Paragraph 22. The method of paragraph 21, wherein the step of reversing rotation is performed after contact between the nose and the far cortex is detected.

Paragraph 23. The method of any one of paragraph 16-18 and 20-22, wherein the nose is configured to bore a smaller hole with similar efficiency when rotated in the first and second directions.

Paragraph 24. The method of paragraph 23, wherein the nose includes a trocar tip.

Paragraph 25. The method of any one of paragraphs 16-24, wherein the implant has a trailing region with a diameter corresponding to a diameter of the larger hole and a leading region with a diameter corresponding to a diameter of the smaller hole, and wherein the step of placing includes a step of placing at least a portion of the trailing region in the larger hole and at least a portion of the leading region in the smaller hole.

Paragraph 26. The method of any one of paragraphs 16-25, wherein the step of placing the implant includes a step of driving the implant into the bone with rotation.

Paragraph 27. The method of any one of paragraphs 16-26, wherein the step of placing the implant includes a step of axially advancing the implant to loosely fit or press fit the implant into the bone.

Paragraph 28. The method of any one of paragraphs 16-27, wherein the step of placing the implant includes a step of attaching the implant to the bone at the larger hole and/or the smaller hole.

Paragraph 29. A method of boring a bone, the method comprising: (A) selecting a drill including a proximal boring portion and a distal boring portion, the proximal boring portion being configured to bore a larger hole in the bone more efficiently when the drill rotates in a first direction compared to an opposite second direction, the distal boring portion being configured to bore a smaller hole in the bone more efficiently when the drill rotates in the second direction compared to the first direction; (B) drilling into the bone with the distal boring portion at a near cortex of the bone as the drill is rotated in the second direction; (C) boring through the near cortex with the proximal boring portion to form the larger hole in the near cortex as the drill is rotated in the first direction; and (D) forming the smaller hole in a far cortex of the bone with the distal boring portion of the drill as the drill is rotated in the opposite second direction.

Paragraph 30. The method of paragraph 29, further comprising a step of reversing rotation of the drill from the second direction to the first direction when the proximal boring portion of the drill closely approaches or contacts the near cortex.

Paragraph 31. The method of paragraph 29 or 30, further comprising a step of reversing rotation of the drill from the first direction to the second direction after the proximal boring portion has passed through the near cortex and before the proximal boring portion contacts the far cortex.

Paragraph 32. The method of paragraph 31, wherein the step of reversing rotation is performed after contact between the distal boring portion and the far cortex is detected.

Paragraph 33. The method of any one of paragraphs 29-32, wherein the step of forming the smaller hole includes a step of advancing the drill along an axis until contact between the proximal boring portion and the far cortex is detected.

Paragraph 34. The method of any one of paragraphs 29-33, further comprising a step of placing an implant at least partially in the bone such that respective regions of the implant are located in the larger hole and the smaller hole.

Paragraph 35. The method of any one of paragraphs 29-34, wherein the step of placing an implant includes a step of attaching the implant to the bone.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. An orthopedic system, comprising:
    a drill including a proximal boring portion and a distal boring portion, the proximal boring portion being configured to bore a larger hole in cortical bone by cutting the cortical bone only when the drill rotates in a first direction, the distal boring portion being configured to bore a smaller hole in the cortical bone by cutting the cortical bone only when the drill rotates in a second direction that is opposite to the first direction; and
    an implant configured to be implanted at least partially in the cortical bone, such that a first region of the implant is located in the larger hole and a second region of the implant is located in the smaller hole.

2. The orthopedic system of claim 1, wherein the first region of the implant has a diameter corresponding to the larger hole, and wherein the second region of the implant has a diameter corresponding to the smaller hole.

3. The orthopedic system of claim 2, wherein at least one of the first region and the second region of the implant has one more external protrusions configured to resist removal of the implant from the cortical bone.

4. The orthopedic system of claim 3, wherein at least one of the first region and the second region of the implant has an external thread or protrusions configured to function as an external thread.

5. The orthopedic system of claim 3, wherein the implant is configured to be driven into the cortical bone by rotation.

6. The orthopedic system of claim 3, wherein the implant has a body from which the one or more external protrusions project, and wherein the body defines the diameter corresponding to that of the larger hole or the diameter corresponding to that of the smaller hole.

7. The orthopedic system of claim 2, wherein the implant is a screw.

8. The orthopedic system of claim 2, wherein the implant is linear.

9. The orthopedic system of claim 1, wherein the implant includes a suture, a wire, a cable, or a combination thereof.

10. The orthopedic system of claim 1, wherein the proximal boring portion of the drill is configured to bore the larger hole when the drill is rotating counterclockwise, and wherein the distal boring portion of the drill is configured to bore the smaller hole when the drill is rotating clockwise.

11. The orthopedic system of claim 1, wherein the proximal boring portion of the drill is configured to bore the larger hole when the drill is rotating clockwise, and wherein the distal boring portion of the drill is configured to bore the smaller hole when the drill is rotating counterclockwise.

12. The orthopedic system of claim 1, wherein the drill includes a nose projecting from a shaft, wherein a leading section of the shaft provides the proximal boring portion, and wherein a leading section of the nose provides the distal boring portion.

13. The orthopedic system of claim 1, wherein the proximal boring portion and/or the distal boring portion has a plurality of cutting edges that are rotationally offset from one another about a long axis of the drill.

14. The orthopedic system of claim 1, wherein the proximal boring portion tapers toward the distal boring portion.

15. The orthopedic system of claim 1, wherein the implant includes a shoulder at a junction between the first region and the second region, wherein the proximal boring portion is configured to form a recess in an inner side of a far cortex of the cortical bone, and wherein the recess is complementary to the shoulder.

* * * * *